US 8,672,480 B2

(12) United States Patent
Isogai et al.

(10) Patent No.: US 8,672,480 B2
(45) Date of Patent: Mar. 18, 2014

(54) OPHTHALMIC PHOTOGRAPHING APPARATUS

(75) Inventors: Naoki Isogai, Nishio (JP); Toshio Murata, Milpitas, CA (US); Mitsuo Yamamoto, Gamagori (JP); Norimasa Satake, Nukata-gun (JP)

(73) Assignee: Nidek Co., Ltd., Gamagori-shi (JP)

( * ) Notice: Subject to any disclaimer, the term of this patent is extended or adjusted under 35 U.S.C. 154(b) by 0 days.

(21) Appl. No.: 13/362,732

(22) Filed: Jan. 31, 2012

(65) Prior Publication Data

US 2012/0127428 A1    May 24, 2012

Related U.S. Application Data

(63) Continuation-in-part of application No. 12/894,551, filed on Sep. 30, 2010, now Pat. No. 8,419,186.

(30) Foreign Application Priority Data

Sep. 30, 2009  (JP) ................... 2009-228768
Feb. 4, 2011   (JP) ................... 2011-023179

(51) Int. Cl.
*A61B 3/14*    (2006.01)
*A61B 3/103*   (2006.01)

(52) U.S. Cl.
USPC ............................. 351/206; 351/205; 351/221

(58) Field of Classification Search
USPC .......................................................... 351/206
See application file for complete search history.

(56) References Cited

U.S. PATENT DOCUMENTS

| 7,506,978 | B2 | 3/2009 | Nanjo |
| 7,510,282 | B2 | 3/2009 | Ueno et al. |
| 7,824,035 | B2 | 11/2010 | Yamada et al. |
| 2007/0091265 | A1* | 4/2007 | Kardon et al. ................. 351/206 |
| 2008/0273172 | A1* | 11/2008 | Spaide ............................ 351/206 |
| 2009/0033870 | A1* | 2/2009 | Hangai et al. ................. 351/206 |
| 2009/0115964 | A1 | 5/2009 | Ueno |

FOREIGN PATENT DOCUMENTS

JP    A-2008-029467    2/2008

OTHER PUBLICATIONS

Office Action issued in U.S. Appl. No. 12/894,551 dated Sep. 5, 2012.

* cited by examiner

*Primary Examiner* — Evelyn A. Lester
*Assistant Examiner* — William Alexander
(74) *Attorney, Agent, or Firm* — Oliff PLC

(57) ABSTRACT

The ophthalmic photographing apparatus includes an optical scanner for two-dimensionally scanning light and an optical coherence tomography device for obtaining a three-dimensional tomographic image of an examiner's eye. The apparatus also includes an observation optical system for obtaining a front observation image of the eye as a moving image and an observation optical system that obtain a front observation image of the examinee's eye as a moving image. The driving control unit controls the optical coherence tomography device based on a signal from an operation unit. A position on the examinee's eye where the tomographic image is picked up is changeable by using the moving image of the front observation image and the analysis map.

7 Claims, 9 Drawing Sheets

OPHTHALMIC PHOTOGRAPHING APPARATUS

This is a continuation-in-Part of application Ser. No. 12/894,551, filed Sep. 30, 2010, now pending.

BACKGROUND OF THE INVENTION

1. Field of the Invention

The present invention relates to an ophthalmic photographing apparatus for photographing a tomographic image of a fundus of an examinee's eye.

2. Description of Related Art

Conventionally, a fundus observation apparatus that obtains a tomographic image of a fundus of an examinee's eye using an optical interference technique (i.e., optical coherence tomography (OCT)) is used for evaluating the condition of the examinee's eye (see Japanese Patent Application Laid-open Publication No. 2008-29467). This kind of fundus observation apparatus controls a monitor to display a fundus image picked up by using infrared light. An examiner selects a given area (portion) of the fundus image and obtains a fundus tomographic image of the selected area. The examiner observes the obtained fundus tomographic image and judges the presence or absence of abnormality in the examinee's eye.

However, a great deal of expertise is required for judging the presence or absence of abnormality in the examinee's eye based on the fundus tomographic image because the fundus tomographic configuration varies depending on the selected area of the fundus image.

In addition, conventionally, an ophthalmic photographing apparatus that obtains a tomographic image of an examinee's eye using an optical interference technique (e.g., a tomographic fundus image) using an optical interference technique (i.e., OCT) is known (see Japanese Patent Application Laid-open Publication No. 2008-29467).

For example, a front image of the fundus that is obtained by using infrared light is displayed on a monitor, and a given area (portion) of the fundus image is selected. Then, a fundus tomographic image of the selected area is obtained by the OCT device, and is stored temporarily in a memory unit (e.g., a hard disk) of a personal computer. Then, the obtained fundus tomographic image is analyzed by the personal computer (PC) or other devices, and a result of the analysis is displayed on the monitor.

However, conventionally, in order to obtain and analyze a three-dimensional tomographic image, numbers of tomographic images are obtained, so that an examiner takes a lot of trouble with identifying the tomographic images of a diseased area of the eye.

SUMMARY OF THE INVENTION

An object of the invention is to overcome the problems described above and to provide an ophthalmic photographing apparatus that is capable of favorably assisting an examiner when a three-dimensional tomographic image is obtained.

To achieve the objects and in accordance with the purpose of the present invention, an ophthalmic photographing apparatus includes an optical coherence tomography device that includes an optical scanner for setting a photographing position on an examinee's eye, and is arranged to obtain a tomographic image of the examinee's eye, a monitor, a driving control unit arranged to control driving of the optical scanner and scan measurement light two-dimensionally on the eye, and obtain a three-dimensional image of the eye, an image processing unit arranged to analyze the three-dimensional image, specify an abnormal portion through image processing, and extract a tomographic image corresponding to the specified abnormal portion from the three-dimensional image, and a display control unit arranged to control the monitor to display the extracted tomographic image corresponding to the abnormal portion.

The present invention allows the examiner to be assisted in obtaining a three-dimensional tomographic image.

Additional objects and advantages of the invention are set forth in the description which follows, are obvious from the description, or may be learned by practicing the invention. The objects and advantages of the invention may be realized and attained by the ophthalmic photographing apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Reference Example

Fundus Observation Apparatus

Figure 1:
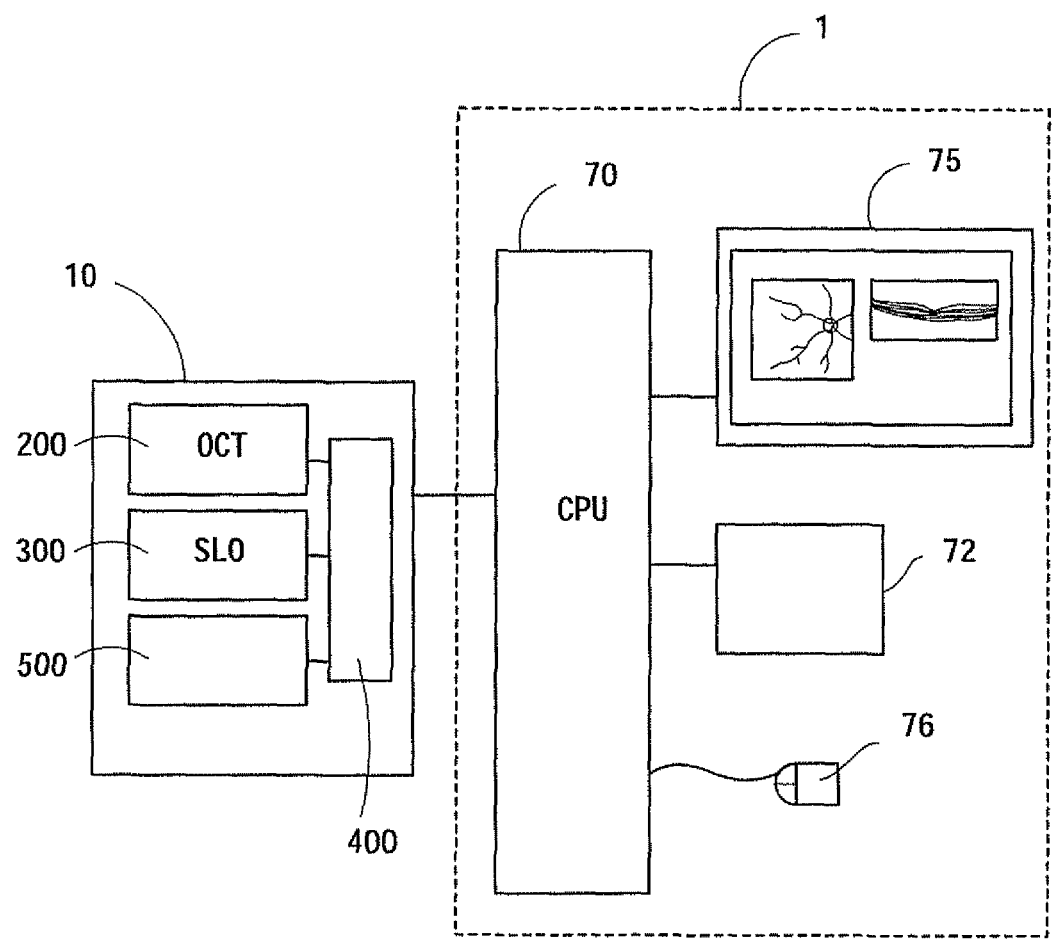
FIG. 1 is a block diagram for explaining the configuration of a fundus observation apparatus of a reference example.

A detailed description of a fundus observation apparatus of a reference example is provided below with reference to the accompanying drawings. FIG. 1 is a block diagram for explaining the configuration of the fundus observation apparatus of the reference example.

A fundus observation apparatus 1 is arranged to observe on a monitor a fundus image obtained by a fundus photographing apparatus 10. The fundus observation apparatus 1 includes a CPU (arithmetic control unit) 70, a mouse (operation input unit) 76, a memory (storage unit) 72, and a monitor 75. These units are connected electrically to the CPU 70 via buses or other mechanisms.

The CPU 70 controls operations of these units under an ophthalmic observation program and various control programs that are stored in the memory 72. By executing the ophthalmic observation program on the computer, the fundus observation apparatus 1 becomes operational. The CPU 70 controls the display screen on the monitor 75 following the ophthalmic observation program. The ophthalmic observation program of the reference example has the function of displaying photographed images and various measurement results on the monitor 75, and an analysis mode function of determining whether a photographed portion is normal or abnormal by analyzing a tomographic image.

It is also preferable that an arithmetic processing unit, an input unit, a storage unit, and a display unit that are included in a commercially available PC (personal computer) are used for the CPU 70, the mouse 76, the memory 72, and the monitor 75, and the ophthalmic observation program is installed on the commercially available PC.

The fundus photographing apparatus 10 arranged to photograph an image of a given portion of an examinee's eye is connected to the fundus observation apparatus 1. As shown in FIG. 1, the fundus photographing apparatus 10 includes an interference optical system (OCT optical system) 200 arranged to obtain a tomographic image of a fundus of the examinee's eye, a front observation optical system 300 arranged to obtain a front image of the fundus, a control unit 400, and a fixation target projection unit 500 capable of fixating the examinee's eye and changing the fixation direction. Thus, the fundus photographing apparatus 10 can photograph a fundus portion of the examinee's eye. For a detailed configuration of the fundus photographing apparatus 10, please refer to Japanese Patent Application Laid-open Publication No. 2008-29467.

The fundus photographing apparatus 10 is arranged to select a given region of the fundus observation image (SLO image) obtained by picking up an image of the fundus, and obtain a fundus tomographic image of the selected region using fundus OCT.

The interference optical system 200 includes a first scanning unit (optical scanner) arranged to scan first measurement light emitted from a first light source on the fundus, and a first photodetector arranged to photo-receive interference light that is obtained by combining reference light resulting from light emitted from the first light source and reflection light of the first measurement light that is projected onto the fundus. Accordingly, the interference optical system 200 has the configuration of a so-called ophthalmic optical coherence tomography (OCT) device. For the configuration of the interference optical system 200, Spectral-domain OCT (SD-OCT) using a spectrometer, Swept-source OCT (SS-OCT) using a wavelength variable light source, or Time-domain OCT (TD-OCT) may be used.

The front observation optical system 300 includes a second scanning unit (optical scanner) arranged to scan second measurement light (e.g., infrared light) emitted from a second light source two-dimensionally on the fundus, and a second photodetector arranged to photo-receive the light reflected from the fundus through a confocal opening disposed at a position substantially conjugate with the fundus. Accordingly, the front observation optical system 300 has the configuration of a so-called ophthalmic scanning laser ophthalmoscope (SLO). For the configuration of the front observation optical system 300, a so-called fundus camera type configuration may be used.

The control unit 400 controls the members of the fundus photographing apparatus 10 to obtain the tomographic image (OCT image) based on a photo-receiving signal outputted from the first photodetector of the interference optical system 200 and obtain the front image (SLO image) based on a photo-receiving signal outputted from the second photodetector of the front observation optical system 300.

The fixation target projection unit 500 includes a visible light source that emits visible light, and is arranged to change the photographed portion by two-dimensionally changing the fixation position of the examinee's eye. The fixation target projection unit 500 may have various configurations such as a configuration that the fixation position is adjusted by using the lighting position of LEDs arranged in a matrix and a configuration that light emitted from a light source is scanned by an optical scanner and the fixation position is adjusted by controlling lighting of the light source.

The fundus observation apparatus 1 and the fundus photographing apparatus 10 are connected to each other on a LAN or other mechanisms, and signals are sent and received therebetween. Various data obtained in the fundus photographing apparatus 10 (e.g., tomographic image data, front image data, various photographing conditions for image obtainment (e.g., image pickup information, selected region information, test date and time)) are transferred to the memory 72 that is a database. The control unit 400 of the fundus photographing apparatus 10 controls the interference optical system 200, the front observation optical system 300, and the fixation target projection unit 500 based on operation signals outputted from the mouse 76.

Descriptions of the operations of the apparatuses having the configurations described above are provided. First, the tomographic image is obtained by using the fundus photographing apparatus 10. As a preliminary preparation to the image obtainment, patient information (e.g., ID number, name, age, sex, major complaint, comments) is inputted. On the monitor 75, the tomographic image obtained by the interference optical system 200, the front image obtained by the front observation optical system 300, and a setting screen for setting the various photographing conditions are displayed.

When an image pickup portion is selected, the control unit 400 controls the fixation target projection unit 500 to move the fixation position to a position corresponding to the selected image pickup portion. For example, when a macula portion photographing mode is selected, the fixation position is set at the center, and when a papilla portion photographing mode is selected, the fixation position is set toward the nose on a slightly upper side. It should be noted that the fixation positions of right and left eyes are substantially symmetrical along the horizontal direction. In the reference example, a targeted image pickup portion and the fixation position provided by the fixation target photographing unit are associated with each other, based on which the fixation position is set. Accordingly, a tomographic image of a fundus portion the examiner desires is easily obtained.

Figure 2:
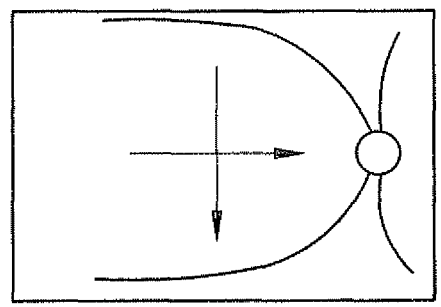
FIG. 2 is a view showing a case where a cross-line scan in horizontal and vertical directions is selected in a macula portion photographing mode.
Figure 3:
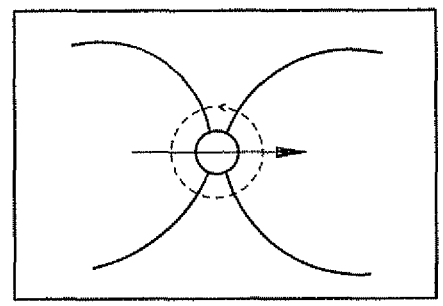
FIG. 3 is a view showing a case where a horizontal line scan or a circle scan is selected in a papilla portion photographing mode.

Then, a scanning pattern of the measurement light (e.g., line, cross-line, raster, circle, radial) is selected. For example, in the macula portion photographing mode, a cross-line scan in the horizontal and vertical directions is selected (see FIG. 2), and in the papilla portion photographing mode, a horizontal line scan or a circle scan is selected (see FIG. 3). Alternatively, multi line photographing shown in FIG. 4 may be performed.

Then, alignment and focusing with respect to the fundus are performed using the front image obtained by the front observation optical system 300. When a trigger of photographing is outputted, the control unit 400 drives the first scanning unit based on the previously set photographing conditions to obtain a tomographic image corresponding to the selected scanning pattern. The obtained tomographic image and the corresponding front image (SLO image), image pickup information (e.g., fixation position information, image pickup portion information, right and left eye information), and selected region information (e.g., scanning pattern, scanning position, scanning range) are stored in the memory 72. The image pickup information described above may be information when the front image corresponding to the tomographic image is obtained.

Then, the tomographic image and the front image that are obtained as described above are observed by using the fundus observation apparatus 1. When an analysis mode is selected, the CPU 70 detects information on retinal layers in the tomographic image stored in the memory 72 through image processing. Then, the CPU 70 analyses the detection result of the retinal layers by a given determination criterion, and determines whether the photographed portion is normal or abnormal. Then, the CPU 70 controls the monitor 75 to display the tomographic image and the determination result.

The determination result may be used as assisting information for assisting the examiner in judging the fundus tomographic image. In such a case, the CPU 70 changes the determination criterion based on at least one of the image pickup information and the selected region information on the fundus tomographic image, and controls the monitor 75 to display the determination result obtained by the changed determination criterion as the assisting information. In other words, the CPU 70 changes information that is to be displayed as the assisting information based on at least one of the image pickup information and the selected region information on the fundus tomographic image.

The detection of the retinal layers is performed such that the CPU 70 analyzes a brightness level of the tomographic image and detects a region corresponding to a given retinal layer (e.g., retinal surface, retinal pigment epithelium layer). In addition, the determination of the photographed portion may include thickness determination of the retinal layers, shape determination, and size determination of the given portion. In addition, a database that stores thicknesses of retinal layers, shapes of given portions, sizes of the give portions of a normal eye may be used as the standard for the image determination criterion.

FIGS. 5A to 5D are views showing specific examples of a determination criterion for analyzing an image obtained in the macula portion photographing mode. In an image of a macula portion, a characteristic image of the retinal surface having a recessed portion at the center is generally obtained. The CPU 70 selects the determination criterion for determining the macula portion based on photographing mode information, and determines the detection result on the retinal layers by the determination criterion.

In the determination of the macula portion image, the CPU 70 determines that the photographed portion is normal if the thickness between the retinal layers is within a given range and the retinal layer shape is normal (see FIG. 5A), and controls the monitor 75 to display the determination result. It should be noted that if the photographed portion is normal, the display is not necessarily performed.

On the other hand, the CPU 70 determines that the photographed portion is abnormal if the retinal layer shape is unusual (for example, the recessed portion is not detected (see FIG. 5B), the retinal layer has an irregular shape (see FIG. 5C)), if the thickness between the retinal layers is out of the given range (see FIG. 5D), or if the retinal layers are not detected, and controls the monitor 75 to display the determination result. For example, a message "the macula portion is abnormal" is displayed. In addition, the CPU 70 may highlight a portion corresponding to the abnormal portion (for example, an image region corresponding to the macula portion is circled). The reason of the determination that the photographed portion is abnormal, for example, the recessed portion cannot be detected, may be displayed.

The CPU 70 may change the determination criterion according to the scanning direction of the measurement light on the fundus, and determine whether the photographed portion is normal or abnormal by the determination criterion. This operation may be used when tomographic images of the same portion (e.g., the macula portion) are obtained in different scanning directions.

Figure 6A:
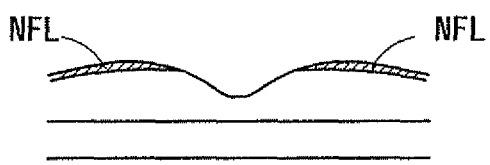
FIGS. 6A and 6B are views showing specific examples of a determination criterion for performing thickness determination on a retinal optic nerve fiber layer (NFL)

For example, this operation may be used when the layer thickness determination is performed on a retinal optic nerve fiber layer (NFL). In the case of determining a vertical line scan image obtained by scanning the measurement light in the vertical (up and down) direction (see FIG. 6A), the CPU 70 determines that the photographed portion is abnormal if, on the image, at least one of thicknesses of the nerve fiber layer that is symmetrically formed on the right side and the left side with respect to the macula portion are out of a given range (also if at least one of the thicknesses are not detected). The CPU 70 determines that the photographed portion is normal if both of the thicknesses of the nerve fiber layer that is symmetrically formed on the right side and the left side with respect to the macula portion are in the given range.

Figure 6B:
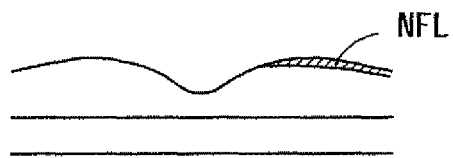

In the case of determining a horizontal line scan image obtained by scanning the measurement light in the horizontal direction (FIG. 6B), the CPU 70 determines that the photographed portion is abnormal if, on the image, the thickness of the nerve fiber layer on the papilla portion side with respect to the macula portion (the right side in a right eye and the left side in a left eye) is out of the given range (also if the thickness is not detected). The CPU 70 determines that the photographed portion is normal if the thickness is within the given range. It should be noted that the CPU 70 does not determine that the photographed portion is abnormal even if the thickness of the nerve fiber layer on the opposite side to the papilla portion with respect to the macula portion is out of the given range (also if the thickness is not detected). In the thickness determination of the nerve fiber layer, the use of the horizontal line scan image may be avoided.

The change of the determination criterion according to the scanning direction and the display of the determination results that the photographed portion is normal or abnormal favorably assist an unaccustomed examiner in performing image diagnosis. The pattern of the nerve fiber layer extending in the retina is symmetric with respect to the macula portion in the vertical direction and is asymmetric with respect to the macula portion in the horizontal direction. Thus, an unaccustomed examiner could judge that the photographed portion is abnormal in a horizontal line scan image in which an image region corresponding to the nerve fiber layer is not visually observed in both of right and left regions. However, the technique described above can prevent the examiner from making such a judgment error.

The present invention is not limited to the scanning patterns described above. It is also preferable that tomographic images that are obtained at given angles (e.g., 30 degrees, 45 degrees) having a given photographed portion at the center are analyzed by different determination criteria. In this case, because the extending pattern of the nerve fiber layer differs according to the scanning direction, the image diagnosis is performed in consideration of this point.

In addition to the determination results, the CPU 70 may control the monitor 75 to display assisting information for assisting the examiner in performing the image diagnosis. In addition, the CPU 70 may control the monitor 75 to display different assisting information according to the scan direction of the measurement light.

For example, in the case of displaying the vertical line scan image (see FIG. 6A), the CPU 70 controls the monitor 75 to display a message "if the eye is normal, the nerve fiber layer is symmetric with respect to the macula portion", or to perform highlight display in the image display. In the case of displaying the horizontal line scan image (see FIG. 6B), the CPU 70 controls the monitor 75 to display a message "even if the eye is normal, the optical fiber layer is asymmetric with respect to the macula portion", or to perform highlight display in the image display.

Figure 7A:
FIGS. 7A and 7B are views showing specific examples of a determination criterion for analyzing an image obtained in the papilla portion photographing mode.
Figure 7B:

FIGS. 7A and 7B are views showing specific examples of a determination criterion for analyzing an image obtained in the papilla portion photographing mode. In an image of a papilla portion, a characteristic image of the papilla portion having a recessed portion at the center that is larger than the macula portion is obtained by the line scan. The CPU 70 selects the determination criterion for determining the papilla portion based on the photographing mode information and the scanning pattern information, and determines the detection result on the retinal layers by the determination criterion. In other words, the CPU 70 changes the determination criterion according to the scanning pattern.

In the determination of a papilla portion image obtained by the line scan, the CPU 70 determines that the photographed portion is normal if the size of the recessed portion (or a C/D ratio of the recessed portion) is within a given range (see FIG. 7A), and controls the monitor 75 to display the determination result. The CPU 70 determines that the photographed portion is abnormal if the size of the recessed portion is out of the given range (see FIG. 7B), and controls the monitor 75 to display the determination result. For example, a message "the papilla portion is abnormal" is displayed. The CPU 70 may determine whether the thickness between or the shape of the retinal layers is normal or abnormal as in the case of the macula portion.

Figure 8A:
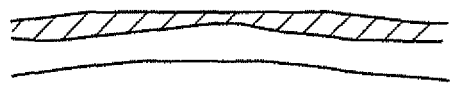
FIGS. 8A and 8B are views showing specific examples of a determination criterion for determining a papilla portion image obtained by the circle scan.
Figure 8B:
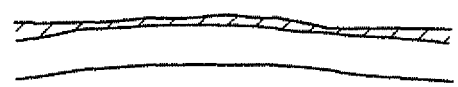

In the determination of a papilla portion image obtained by the circle scan, the CPU 70 determines that the photographed portion is normal if the thickness of the nerve fiber layer is within a given range (see FIG. 8A), and controls the monitor 75 to display the determination result. The CPU 70 determines that the photographed portion is abnormal if the thickness of the nerve fiber layer is out of the given range (see FIG. 8B), and controls the monitor 75 to display the determination result.

As described above, whether the photographed portion is normal or abnormal can be properly determined by changing the determination criterion according to the image pickup portion information. Thus, an examiner who lacks special knowledge about the image diagnosis based on the tomographic image can easily judge whether the photographed portion is normal or abnormal based on the tomographic image.

By performing the line scan or the raster scan at a plurality of different positions on the fundus and obtaining a plurality of tomographic images by the fundus photographing apparatus 10, a wide range tomographic image is obtained. The CPU 70 may specify an image (or a plurality of images) including a characteristic portion from among the obtained plurality of images, and perform the image determination described above.

Figure 4:
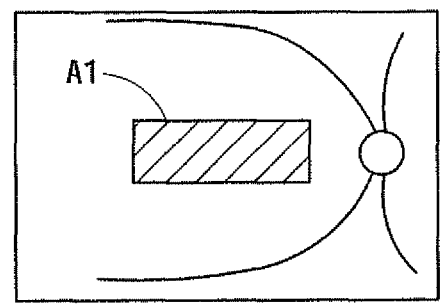
FIG. 4 is a view showing a case where multi line photographing is performed.
Figure 5A:
FIGS. 5A to 5D are views showing specific examples of a determination criterion for analyzing an image obtained in the macula portion photographing mode.
Figure 5B:
Figure 5C:
Figure 5D:
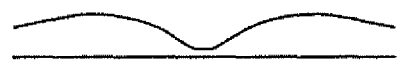

For example, the control unit 400 controls the driving of the first scanning unit to perform the multi line scan (or the raster scan) within a given region A1 as shown in FIG. 4. Thus, a plurality of tomographic images including the macula portion are obtained. The obtained plurality of tomographic images are stored in the memory 72 and are observed by the fundus observation apparatus 1.

The CPU 70 detects the sizes of the recessed portions in the tomographic images, selects one (or more) of the tomographic images in which the recessed portion is largest as an image for the analysis based on the detection result, and shifts to the analysis described above. Then, the CPU 70 determines whether the photographed portion is normal or abnormal. With this technique, the position of the photographed portion is accurately specified even if the position of a targeted image pickup portion is different among individuals, which allows the examiner to perform the image diagnosis adequately.

The present invention is not limited to the technique described above. The CPU 70 may analyze each of the plurality of tomographic images, perform the determination of the presence or absence of the abnormal portion and the specification of the position of the abnormal portion through image processing, and control the monitor 75 to display the results.

Figure 9:
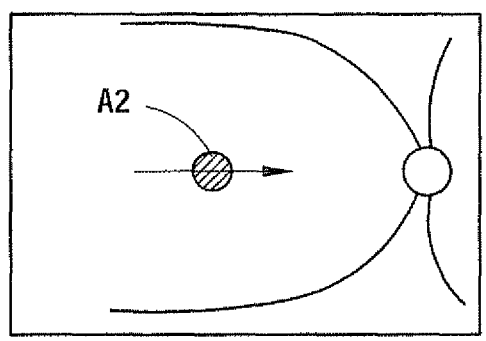
FIG. 9 is a view showing a specific example of a determination criterion for analyzing a front image.

In the configuration described above, the CPU 70 may determine the abnormal portion by analyzing the front image obtained by the front observation optical system 300. FIG. 9 is a view showing a specific example of a determination criterion for analyzing the front image. In the front image, the abnormal portion appears as a brightness change (bright and dark) that does not appear in a normal eye (see a region A2 in FIG. 9).

The CPU 70 selects a determination criterion for determining the front image and performs determination of the presence or absence of the brightness change by the determination criterion. For example, in the determination of the front image, the CPU 70 detects a portion having a brightness level lower than a given level or a portion having a brightness level higher than the given level through image processing, and performs the determination of the presence or absence of the abnormal portion and the specification of the position of the abnormal portion.

Adjustment of Image Pickup Position Based on Tomographic Image Analysis

The fundus photographing apparatus 1 may obtain a tomographic image of a desired portion by performing the analysis described above. For example, the control unit 400 may analyze the tomographic image obtained by the interference optical system 200, specify a targeted image pickup portion through image processing, and adjust the image pickup position so as to obtain an image of the targeted image pickup portion.

In this case, the control unit 400 successively obtains and analyses the tomographic images while adjusting the scanning position of the first scanning unit (an oscillation angle, the center position of the oscillation angle) in order that the scanning position of the measurement light on the fundus may correspond to the position at which a characteristic image (e.g., an image having a characteristic shape as the image pickup portion) is obtained.

For example, the control unit 400 controls the driving of the first scanning unit to perform the multi line scan or the raster scan. Then, the control unit 400 adjusts the image pickup position so as to obtain the tomographic image having the recessed portion corresponding to the macula portion at the center. In this case, the control unit 400 detects the sizes of the recessed portions in the successively obtained tomographic images. If the control unit 400 determines that the tomographic image having the recessed portion corresponding to the macula portion is obtained based on the detection result, the control unit 400 fixes the scanning position of the measurement light. Then, the control unit 400 successively obtains the tomographic images at the scanning position and outputs the images as a moving image (e.g., live image).

In the configuration described above, the control unit 400 performs the determination whether the photographed portion is normal or abnormal and the specification of the position of the abnormal portion through image processing while successively obtaining and analyzing the tomographic images. The control unit 400 may control the driving of the first scanning unit to obtain the tomographic image of the abnormal portion.

Figure 10A:
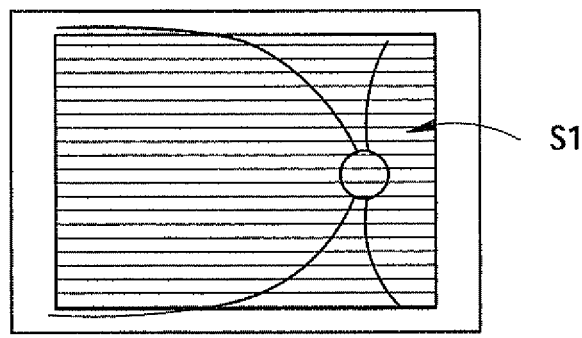
FIGS. 10A to 10C are views for explaining adjustment of an image pickup position based on wide range tomographic image analysis.
Figure 10B:
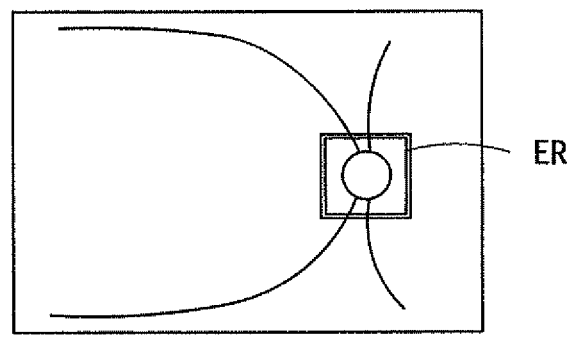
Figure 10C:
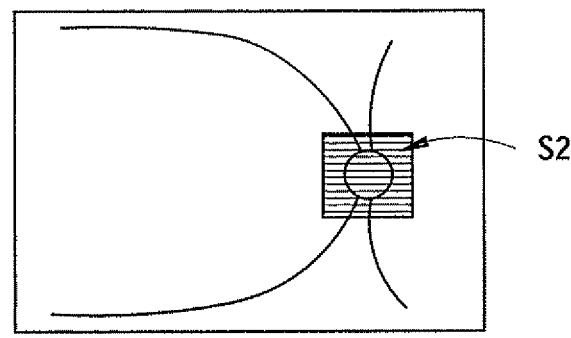

Screening Using Wide Range Tomographic Image and Obtainment of Tomographic Image of Abnormal Portion FIGS. 10A to 10C are views for explaining adjustment of the image pickup position based on wide range tomographic image analysis. For example, the control unit 400 controls the driving of the first scanning unit to scan the measurement light two-dimensionally in a wide range of the fundus and obtain a wide range tomographic image of the fundus (a first tomographic image) (see a hatched portion S1 in FIG. 10A, for example). In this case, it is preferable that the scanning range is set such that the macula portion and the papilla portion are included in the photographing range (e.g., a rectangular region 9 mm long and 9 mm wide, a rectangular region 12 mm long and 12 mm wide). For the scanning pattern, the multi line scan or the raster scan is used, for example. Thus, a plurality of tomographic images that provide fundus tomographic information in the wide range can be obtained.

Next, the control unit 400 specifies the abnormal portion by analyzing the obtained first tomographic image through image processing (first analysis). The control unit 400 may perform analysis appropriate to each of the retinal portions in the tomographic image or may analyze the whole first tomographic image by one criterion (details are provided later).

The control unit 400 outputs the obtained first tomographic image and the front image that is obtained substantially concurrently with the first tomographic image on the monitor 75, and outputs a result of the first analysis on the monitor 75. The control unit 400 may successively drive the interference optical system 200 and the front observation optical system 300 and control the monitor 75 to display a graphic showing the analysis result (for example, display a mark at a portion corresponding to the abnormal portion) in the state of being superimposed on the tomographic observation images and the front observation image that are obtained in real time as moving images (see a mark ER in FIG. 10E). Thus, the examiner is allowed to check the abnormal portion based on the observation images during examination.

Next, the control unit 400 sets a region that is specified to be the abnormal portion as a scanning range of the measurement light and controls the driving of the first scanning unit to obtain a second tomographic image (see a hatched portion S2 in FIG. 10C). The control unit 400 may set the scanning range by obtaining the scanning position corresponding to the region that is specified to be the abnormal portion (the driving position of the first scanning unit) based on the relation between the first tomographic image and the scanning position.

In the case of obtaining the second tomographic image, it is preferable to use the scanning pattern that is suitable for the image obtainment of the abnormal portion. In addition, it is preferable that the scanning range of the second tomographic image is narrower than the scanning range of the first tomographic image (the wide range tomographic image) of the fundus and includes the whole abnormal portion. For example, the raster scan is performed on a rectangular region that is adjusted to the size of the abnormal portion. In addition, the fixation position is preferably set at a position that is suitable for the image obtainment of the abnormal portion. It is also preferable that a plurality of tomographic images are obtained at the same abnormal portion and an averaged image thereof is obtained.

In the case of obtaining the second tomographic image, the control unit 400 may automatically shift to the obtainment of the second tomographic image based on the analysis result of the first tomographic image, or may start the obtainment of the second tomographic image using an operation signal from the mouse 76 as a trigger.

If a plurality of abnormal portions are detected, the control unit 400 obtains the second tomographic image in a scanning range that is narrower than the scanning range of the wide range tomographic image and includes the plurality of abnormal portions. In addition, the control unit 400 may set scanning ranges for the abnormal portions and obtain tomographic images of the abnormal portions successively.

Analysis Appropriate to Each of Retinal Portions

In the case of performing analysis appropriate to each of the retinal portions, the control unit 400 specifies regions corresponding to the macula portion and the papilla portion in the obtained tomographic images through image processing. Then, the control unit 400 performs analysis appropriate to each of the specified regions. When the macula portion is specified, the control unit 400 analyses the macula portion in the tomographic images by using the analysis technique used in the macula portion photographing mode described above. If the papilla portion is specified, the control unit 400 analyses the papilla portion in the tomographic images by using the analysis technique used in the papilla portion photographing mode described above.

In the case of specifying the given portion in the tomographic image, the macula portion and the papilla portion can be extracted based on positions, brightness values, and shapes in the tomographic image. For the macula portion that has brightness lower than that of its peripheral portion and has a circular shape, image processing is performed so as to extract an image region that shows these properties. For the papilla portion that has brightness higher than that of its peripheral portion and has a circular shape, image processing is performed so as to extract an image region that shows these properties. It is also preferable that the positions of the macula portion and the papilla portion are specified by using the front image, and the results are used for the analysis of the tomographic image.

For example, if the CPU 70 determines that the papilla portion is abnormal, the control unit 400 sets the papilla portion as the scanning range of the measurement light and controls the driving of the first scanning unit to obtain the tomographic image of the papilla portion. The scanning range is set to be narrower than the scanning range of the wide range tomographic image described above and to include the whole papilla (for example, 4.5 mm long and 4.5 mm wide). For the papilla portion, the circle scan or the radial scan may be performed.

Analysis on Whole Fundus

In the case of analyzing the whole tomographic images by one criterion, the control unit 400 calculates the thicknesses of the retinal layers (e.g., retinal surface layer, retinal pigment epithelium layer) in the tomographic images. The control unit 400 two-dimensionally obtains a position at which the thickness is out of the given range. A result of comparison between the layer thicknesses of the examinee's eye and layer thicknesses of a normal eye with respect to the horizontal and vertical directions may be used. In addition, the sum of the layer thicknesses may be used in the layer thickness analysis.

The control unit 400 sets the abnormal portion as the scanning range of the measurement light, and controls the driving of the first scanning unit to obtain the tomographic image of the abnormal portion. The scanning pattern that is suitable for the image obtainment of the abnormal portion is preferably used.

With the configuration described above, the two-dimensional tomographic image obtained in the wide scanning range is analyzed, and the abnormal portion in the whole fundus is specified, so that the tomographic image can be obtained with the photographing conditions suitable for the abnormal portion. Because the scanning range is narrower than the wide scanning range and includes the whole fundus, deviation between the images is minimized, and the tomographic image of the abnormal portion can be obtained with high resolution.

The control unit 400 analyzes the second tomographic image (second analysis) and outputs the analysis result on the monitor 75. Thus, a precise analysis result of the abnormal portion is obtained. In this case, the specification and the analysis of the abnormal portion on the fundus can be smoothly performed by specifying the abnormal portion through screening on the whole fundus and precisely analyzing the abnormal portion.

The control unit 400 outputs the second tomographic image and the front image that is obtained substantially concurrently with the second tomographic image on the monitor 75, and outputs the result of the second analysis on the monitor 75. In addition, the control unit 400 outputs the first tomographic image and the second tomographic image on the monitor 75. At least one of the first tomographic image and the second tomographic image may be displayed in the form of a three-dimensional tomographic image.

Correction of Positional Deviation Between First Tomographic Image and Second Tomographic Image In the configuration described above, the control unit 400 may correct the image pickup position of the tomographic image by obtaining the fundus front image that is obtained concurrently with the first tomographic image and calculating a positional deviation between the above fundus front image and the fundus front image that is obtained concurrently with the second tomographic image. The front image may be an image that is obtained by using data forming a two-dimensionally obtained tomographic image (e.g., an integrated image of tomographic images in the depth direction, an integrated value of spectral data at positions in the horizontal and vertical directions).

In addition, the control unit 400 may perform matching between the tomographic image corresponding to the abnormal portion in the first tomographic image and the tomographic images that are continually obtained when obtaining the second tomographic image through image processing, and correct the scanning position so as to obtain the tomographic image at a substantially matching position (the front image may be used instead of the tomographic image). For example, the image of the abnormal portion in the first tomographic image is set as a template image, and template matching is performed between the tomographic images continually obtained and the template image. The scanning position is adjusted so that a correlation may become highest.

Screening Using Wide Range Tomographic Image and Obtainment of Tomographic Image of Characteristic Portion The above descriptions have been given on the case where the tomographic image of the abnormal portion is obtained. However, it is essential only that a tomographic image of a given portion in a wide range tomographic image be obtained by a screening scan.

For example, the control unit 400 may specify a characteristic portion (e.g., papilla portion, macula portion) by analyzing the obtained first tomographic image through image processing, and adjust the image pickup position so as to obtain a tomographic image of the specified characteristic portion. As for the technique of specifying the given portion in the tomographic image, please refer to "ANALYSIS APPROPRIATE TO EACH OF RETINAL PORTIONS" provided above.

Selective Storing of Tomographic Images

The control unit 400 may control the driving of the first scanning unit to perform the multi line scan or the raster scan, and store only the tomographic images that do not meet the given image determination criterion and are determined to be abnormal in the memory 72.

Adjustment of Image Pickup Position Based on Front Image Analysis

The control unit 400 may analyze the front image obtained by the front observation optical system 300, perform the determination of the presence or absence of the abnormal portion and the specification of the position of the abnormal portion, and adjust the image pickup position by the interference optical system 200 so as to obtain the tomographic image of the abnormal portion. The technique of the determination is the same as that of the front image analysis, and descriptions thereof are omitted. Accuracy in specifying the abnormal portion is improved by specifying the abnormal portion based on both of the analysis result on the tomographic image and the analysis result on the front image, and adjusting the image pickup position.

When the abnormal portion is specified, the control unit 400 obtains the tomographic image by controlling the driving of the first scanning unit in order that the scanning position of the measurement light on the fundus may correspond to the abnormal portion (e.g., the portion A2 in FIG. 9).

When the scan is performed on the abnormal portion, the control unit 400 may control the fixation target projection unit 500 with the driving position of the optical scanner being fixed, and guide a line of sight of the examinee's eye by moving the fixation position.

When the image obtainment, the analysis, and the determination are finished, the obtained images, the analysis results, and the photographing conditions (the image pickup information, the selected range information) are stored in association with the patient information. This information can be used as information for performing alignment with respect to the same portion at the time of re-photographing. In other words, the CPU 70 controls the memory 72 to store the photographing conditions including the fixation position (photographed portion) and the image pickup position (scanning position) in association with the photographed images, and reconstitute the photographing conditions at the time of re-photographing.

The alignment may be performed using the shape in the stored retinal layer detection result as a characteristic. In this case, the control unit 400 detects the shape in the tomographic image stored in the memory 72 and successively analyzes tomographic images obtained by the interference optical system 200. The control unit 400 may control the driving of the first scanning unit based on the analysis result and the detection result, and adjust the image pickup position so as to obtain tomographic images of the same portion that has the shape in the detection result.

In the above configuration, the analysis is performed using the two-dimensional tomographic image. However, the present invention is not limited thereto. The analysis may be performed using a three-dimensional image. In this case, determination whether a three-dimensional shape include a characteristic shape or not is performed.

PREFERRED EMBODIMENTS OF THE PRESENT INVENTION

Ophthalmic Photographing Apparatus

Figure 11:
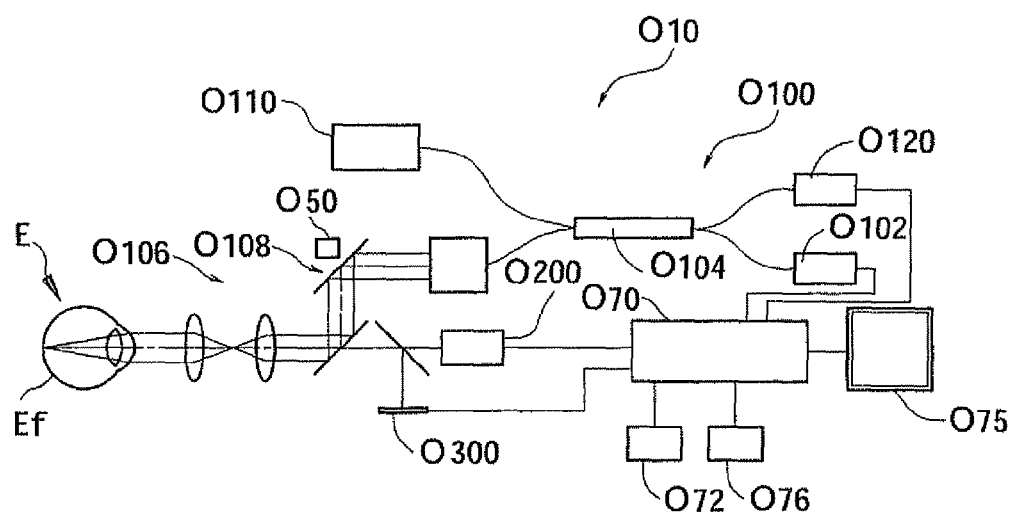
FIG. 11 is a view showing a schematic configuration for explaining the configuration of an ophthalmic photographing apparatus of a preferred embodiment of the present invention.

Next a detailed description of an ophthalmic photographing apparatus of preferred embodiments of the present invention is provided below with reference to the accompanying drawings. FIG. 11 is a view showing a schematic configuration for explaining the configuration of the ophthalmic photographing apparatus of the preferred embodiments of the present invention. In the present embodiments, an axial direction of an examinee's eye (eye E) is referred to as a Z-direction, a horizontal direction of the eye E is referred to as an X-direction, and a vertical direction of the eye E is referred to as a Y-direction. A surface direction of a fundus of the eye E may be regarded as an XY-direction.

A brief description of the configuration of the apparatus is provided. The present apparatus defines an optical coherence tomography device (OCT device) O10 for photographing a tomographic image of a fundus Ef of the eye E. The OCT device O10 includes an interference optical system (OCT optical system) O100, a front observation optical system O200, a fixation target projection unit O300, and an arithmetic control unit (CPU) O70.

The OCT optical system O100 is arranged to project measurement light onto the fundus. The OCT optical system O100 is arranged to detect the state of interference of the measurement light reflected from the fundus and reference light with the use of a photodetector (detector O120). The OCT optical system O100 includes a projection position changing unit (e.g., an optical scanner O108, the fixation target projection unit O300) arranged to change a projection position of the measurement light onto the fundus Ef in order to change a image pickup position on the fundus at which the fundus image is picked up. The control unit O70 is arranged to control the operation of the projection position changing unit based on information on the set image pickup position, and obtain a tomographic image based on a photo-receiving signal from the detector O120.

<OCT Optical System>

The OCT optical system O100 has a configuration of a so-called ophthalmic optical coherence tomography (OCT) device, and is arranged to pick up a tomographic image of the eye E. The OCT optical system O100 divides light emitted from measurement light source O102 into measurement light (sample light) and reference light with the use of a coupler (light divider) O104. Then, the OCT optical system O100 directs the measurement light to the fundus Ef of the eye E with the use of a measurement optical system O106, and directs the reference light to a reference optical system O110. Then, the OCT optical system O100 photo-receives interference light that is obtained by combining the measurement light reflected from the fundus Ef and the reference light with the use of the detector (photodetector) O120.

The detector O120 is arranged to detect the state of interference of the measurement light and the reference light. In using a Fourier domain OCT, spectral intensity of the interference light is detected by the detector O120, and a depth profile (an A scan signal) in a given range is obtained by performing Fourier transform on data on the spectral intensity. Examples of the Fourier domain OCT include a spectral-domain OCT (SD-OCT), and a swept-source OCT (SS-OCT). It may be a time-domain OCT (TD-OCT).

In using the SD-OCT, a low coherent light source (broad-band light source) is used as the measurement light source O102, and the detector O120 is provide with a spectral optical system (spectral meter) arranged to divide the interference light into various frequency components (wavelength components). The spectral meter includes a diffraction gratin and a line sensor.

In using the SS-OCT, a wavelength scanning light source (wavelength-variable light source) that is arranged to vary the wavelength of the emitted light is used as the light source O102, and a single photodetector is used as the detector O120. The light source O102 preferably includes a light source, a fiber ring resonator and a wavelength-selecting filter. Examples of the wavelength-selecting filter include a combination of a diffraction gratin and a polygon mirror, a wavelength-selecting filter using a Fabry-Perot etalon.

The light emitted from the light source O102 is divided into the measurement light and the reference light by the coupler O104. Then, the measurement light is emitted into the air after passing through an optical fiber. The measurement light passes through the optical scanner O108 and other optical members of the measurement optical system O106, and is collected on the fundus Ef. The light reflected from the fundus Ef passes through the same path and goes back to the optical fiber.

The optical scanner O108 scans the measurement light in the XY-direction (transverse direction) on the fundus. The optical scanner O108 is disposed at a position substantially conjugate with a pupil of the eye. The optical scanner O108 defines two galvano-mirrors, and its reflection angle is arbitrarily adjusted with the use of a driving mechanism O50.

Thus, the reflection (travelling) direction of the light emitted from the light source O102 is changed, and scanned on the fundus in a given direction. Thus, the position on the fundus Ef at which an image is to be picked up is changed. It is essential only that the optical scanner O108 should have a configuration so as to deflect light. Examples of the optical scanner O108 include a reflection mirror (a galvano-mirror, a polygon mirror, a resonant scanner), and an acoustic optical element (AOM) that is arranged to change a travelling (deflection) direction of light.

The reference optical system O110 is arranged to generate the reference light that is to be synthesized with the measurement light reflected from the fundus Ef. The reference optical system O110 may be of a Michelson type, or of a Mach-Zehnder type. The reference optical system O110 includes a reflection optical system (e.g., a reference mirror), and is arranged to return the light to the coupler O104 by reflecting the light from the coupler O104 with the use of the reflection optical system, and direct the light to the detector O120. It is also preferable that the reference optical system O110 includes a transmissive optical system (e.g., an optical fiber), and is arranged to transmit the light without returning it to the coupler O104, and direct the light to the detector O120.

The reference optical system O110 is arranged to change a difference between an optical path of the measurement light and an optical path of the reference light by moving an optical member on the optical path of the reference light. For example, the reference mirror is moved in an optical axis direction. The difference between the optical paths can be changed also by a member disposed on the optical path of the measurement light in the measurement optical system O106.

<Front Observation Optical System>

The front observation optical system O200 is arranged to obtain a front image of the fundus Ef. The front observation optical system O200 includes an optical scanner arranged to scan measurement light (e.g., infrared light) emitted from a light source two-dimensionally on the fundus, and a second photodetector arranged to photo-receive the light that is reflected from the fundus and passes through a confocal opening disposed at a position substantially conjugate with the fundus. The front observation optical system O200 has a configuration of a so-called ophthalmic scanning laser ophthalmoscope (SLO).

For the configuration of the front observation optical system O200, a so-called fundus camera type configuration may be used. In addition, the OCT optical system O100 functions also as the front observation optical system O200. To be specific, the front image may be obtained by using data forming a two-dimensionally obtained tomographic image (e.g., an integrated image of three-dimensional tomographic images in the depth direction, an integrated value of spectral data at positions in the XY-directions, intensity data in a uniform depth direction at positions in the XY-directions, a retinal surface image).

<Fixation Target Projection Unit>

The fixation target projection unit O300 includes an optical system arranged to guide a visual line direction of the eye E. The fixation target projection unit O300 includes a fixation target to present to the eye E, and is capable of guiding the eye E in a plurality of directions.

For example, the fixation target projection unit O300 includes a visible light source that emits visible light, and is arranged to two-dimensionally change the position to present the target. Thus, the visual line direction is changed, whereby the portion at which an image is to be picked up is changed. For example, if the target is presented from the direction same as a photographing optical axis, a center portion of the fundus is established as the portion at which an image is to be picked up. Alternatively, if the target is presented above the photographing optical axis, an upper portion of the fundus is established as the portion at which an image is to be picked up. That is, the portion at which an image is to be picked up is changed in accordance with the position of the target with respect to the photographing optical axis.

The fixation target projection unit O300 may have various configurations such as a configuration that the fixation position is adjusted by lighting position of LEDs arranged in a matrix, and a configuration that light emitted from a light source is scanned by an optical scanner and the fixation position is adjusted by controlling lighting of the light source. The fixation target projection unit O300 may be of an internal fixation lamp type or an external fixation lamp type.

<Control Unit>

The control unit O70 controls the members O100 to O300, and thus controls the entire apparatus. The control unit O70 functions also as an image processing unit arranged to process the obtained image, and an image analysis unit arranged to analyze the obtained image. A generally-used CPU (Central Processing Unit) is preferably used as the control unit O70. The control unit O70 analyzes the fundus Ef based on the tomographic image as described below.

The control unit O70 obtains the tomographic image (OCT image) through image processing based on a photo-receiving signal outputted from the photodetector O120 of the OCT optical system O100, and obtains the front image (SLO image) based on a photo-receiving signal outputted from the photodetector of the front observation optical system O200. In addition, the control unit O70 controls the fixation target projection unit O300 to change the fixation position.

A memory (storage unit) O72, a monitor (display unit) O75 and an operation unit O76 are connected electrically to the control unit O70. The control unit O70 controls a display screen of the monitor O75. The obtained fundus image is outputted as a still image or a moving image to the monitor O75, and stored in the memory O72. The memory O72 records the photographed tomographic image and front image, and various photographing information on the photographing positions of the tomographic images. The control unit O70 controls the OCT optical system O100, the front observation optical system O200, and the fixation target projection unit O300 based on operation signals outputted from the operation unit O76. A touch panel is preferably used as the monitor O75, and used for various operations including setting of a scanning position and a fixation position. For a detailed configuration of the OCT device O10, please refer to Japanese Patent Application Laid-open Publication No. 2008-29467.

<Obtainment of Tomographic Image>

Figure 12:
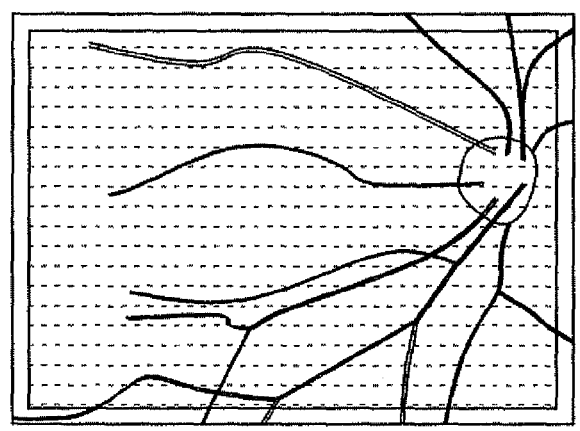
FIG. 12 is a view showing an example of a fundus front image obtained by an observation optical system.

As shown in FIG. 12, the control unit O70 controls the OCT optical system O100 to obtain a three-dimensional tomographic image corresponding to an established area, and controls the front observation optical system O200 to obtain a fundus front image. Then, the control unit O70 controls the OCT optical system O100 to obtain a three-dimensional tomographic image, and controls the front observation optical system O200 to obtain a fundus front image, as needed. Examples of the three-dimensional tomographic image include image data of A-scan signals arranged two-dimensionally in the XY-directions, and a three-dimensional graphic image.

In obtaining the three-dimensional tomographic image, the control unit O70 controls the operation of the optical scanner O108, and scans the measurement light two-dimensionally in the XY-directions in a scanning area corresponding to the image pick-up area, whereby the three-dimensional tomographic image is obtained. Examples of a scanning pattern include a raster scan and a multi line scan.

<Determination of Photographed Portion>

Figure 13:
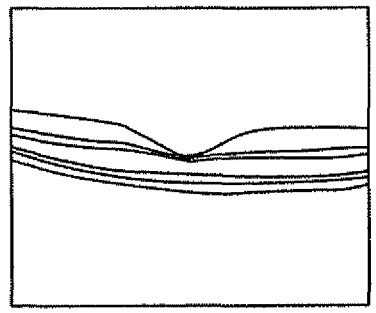
FIG. 13 is a view showing an example of a tomographic image obtained by an OCT optical system.

FIG. 13 is a view showing an example of the tomographic image obtained by the OCT optical system O100. The control unit O70 includes an image analysis unit, and detects information on layers of the fundus in the obtained tomographic image (e.g., three-dimensional tomographic image) through image processing. The control unit O70 analyzes detection results of the layers based on a given image determination condition (determination criterion), and determines whether the photographed portion is normal or abnormal. Then, the control unit O70 obtains an analysis result of the tomographic image based on the determination results. Then, the analysis result is stored in the memory O72 or an external memory (e.g., a memory of a personal computer, a memory of a server) together with the tomographic image.

The detection of the layers is performed such that a brightness level of the tomographic image is detected, and boundaries of layers corresponding to given retinal layers (e.g., a retinal surface and a retinal pigment epithelium layer) are extracted through image processing. Then, spaces of the boundaries are measured, and thus the thicknesses of the layers are measured.

The determination of the tomographic image may include thickness determination of the layers, shape determination, and size determination of a given portion (e.g., a papilla portion, a macular portion). A normal eye database that stores spaces between layers, shapes of given portions, sizes of the give portions of a normal eye is used as the standard for the image determination condition. The normal eye database is stored in the memory O72.

For example, the control unit O70 measures the thicknesses at the portions in the transverse direction, and determines whether the measurement results fall within a given range in the normal eye database (e.g., within a normal range corresponding to the measurement values of the normal eye). Then, the control unit O70 determines that the portion, of which the thickness is determined to fall within the normal range, is normal. On the other hand, the control unit O70 determines that the portion, of which the thickness is determined to go beyond the normal range, is abnormal. Thus, an abnormal portion in the tomographic image is specified.

Then, the control unit O70 calculates the thicknesses of retinal layers (e.g., a retinal surface and a retinal pigment epithelium layer) of each tomographic image. Then, the control unit O70 two-dimensionally obtains the portion of which the thickness goes beyond the given range. It is also preferable that a result of comparison between the layer thicknesses of the examinee's eye and the layer thicknesses of the normal eye in the XY-directions is used. It is also preferable that in the analysis using the layer thicknesses, a total value of the layer thicknesses is used.

Figure 14:
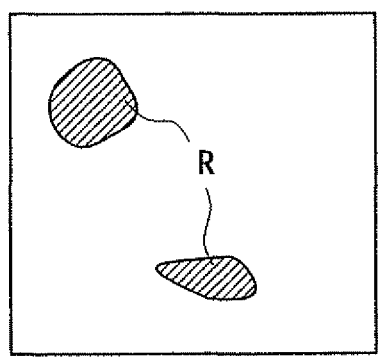
FIG. 14 is a view showing a result of analysis of the tomographic image.

FIG. 14 is a view showing the analysis result of the tomographic image, which is an example of a map (hereinafter, referred to as an analysis map) that two-dimensionally indicates abnormal portions at position on the fundus. In the present embodiments, the control unit O70 makes up an analysis map that indicates the analysis result of the three-dimensional tomographic image in graphics based on the analysis result obtained as described above. The analysis map indicates two-dimensional distribution data on the normal/abnormal portions, for example.

After making up the analysis map, the control unit O70 displays the analysis map on the monitor O75. For example, the control unit O70 displays graphics (see the hatched areas R) indicating the abnormal portions as shown in FIG. 14. For example, the hatched areas R are displayed in a specific color (e.g., red). It is also preferable that the control unit O70 displays the abnormal portions by surrounding them with a marker. It is also preferable that the control unit O70 displays the abnormal portions in graphics that are identifiable. It is also preferable that the control unit O70 makes up a layer thickness map as the analysis map, which indicates two-dimensional distribution of the layer thicknesses based on the information on the layers of the fundus that is detected as described above (e.g., a map indicating the layer thicknesses of the fundus, a map indicating a difference from data on a normal eye).

The analysis result of the tomographic image contains measurement information based on the tomographic image, a determination result based on the measurement information, disease information based on the tomographic image, and positional information on the abnormal portion on the fundus.

In the case of determining the stage of development of glaucoma in the analysis described above, it is preferable that the thicknesses of a retinal optic nerve fiber layer and a ganglionic cell lamina are measured, and measurement results are compared with the normal eye database, whereby an abnormal portion is specified. In this case, it is also preferable that the thicknesses between the retinal optic nerve fiber layer, the ganglionic cell lamina, and an inner pellicle layer are measured and analyzed.

Examples of the measurement information include a layer thickness, a shape and a size of a give portion, and an area, a volume and a width of a region where the layer thickness goes beyond a normal value. Examples of the determination results include a result of comparison between the measurement result of the tomographic image and the normal eye database (e.g., a result of comparison between the layer thickness information of the fundus tomographic image and the normal eye database), and a map image based on the comparison result. Examples of the disease information include a name of a disease of tan examinee, and the stage of development of a disease.

In the case of obtaining the analysis result, a result may be used, which is obtained by an examiner by specifying an abnormal portion based on the tomographic image, in addition to the result of the analysis through image processing described above.

<Explanation of Operation>

Figure 15:
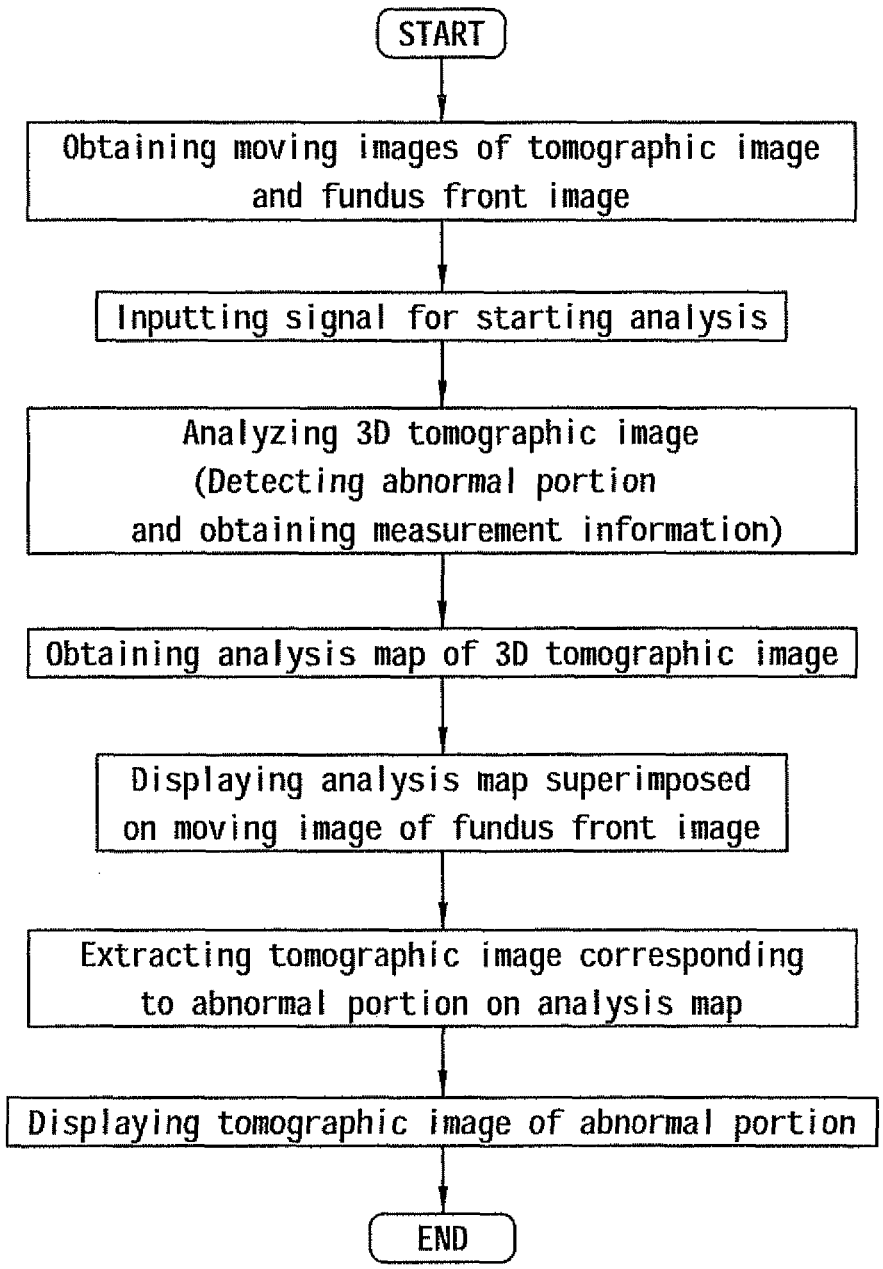
FIG. 15 is a flow chart for explaining the procedure of operation of the apparatus.

A description of the operation of the apparatus having the configuration described above will be provided with referent to the flow chart shown in FIG. 15. The control unit O70 controls the front observation optical system O200 to obtain a live moving image of the front observation image of the examinee's eye, and controls the monitor O75 to display both the live moving image of the front observation image and a still image of a tomographic image that is extracted from the three-dimensional tomographic image, at the same time (see FIG. 16).

The control unit O70 controls the driving of the OCT optical system O100 and the driving of the front observation optical system O200 to obtain frames of the three-dimensional tomographic image and the fundus front image (SLO image). Then, the control unit O70 controls the monitor O75 to renew the display of the three-dimensional tomographic image and the fundus front image as needed.

<Analysis Processing>

If the examiner manipulates a photographing switch (not shown) at this time to input a signal for starting analysis, the control unit O70 starts analysis processing of the three-dimensional tomographic image. Analyzing the three-dimensional tomographic image through image processing, which is obtained after the output of the starting signal, the control unit O70 specifies an abnormal portion and obtains measurement information. For example, the control unit O70 performs determination of the three-dimensional tomographic image through image processing with the use of the determination criterion described above. Then, the control unit O70 specifies the abnormal portion on the fundus Ef based on a determination result.

Described in the present embodiments is the configuration that the input of the starting signal through the manipulation of the photographing switch (not shown) starts the analysis processing of the tomographic image; however, the present invention is not limited to this configuration. For example, a configuration is preferable such that obtainment of an interference signal corresponding to the fundus Ef in the interference signals outputted from the detector O120 triggers the control unit O70 to automatically start the analysis processing of the tomographic image. Thus, the analysis processing of the tomographic image is started more smoothly.

For example, when the difference between the optical path lengths is adjusted and the interference signal corresponding to the fundus Ef is obtained, the control unit O70 starts the analysis processing of the obtained tomographic image. The presence or absence of an interference signal corresponding to the layer of the fundus is determined based on intensity distribution of the interference signals. It is also preferable that detection of an image corresponding to a papilla portion or a central fovea inputs the starting signal. In this case, the presence or absence of a papilla portion or a central fovea is determined based on the obtained tomographic image.

<Obtainment of Analysis Map, and Superimposed Display>

Next, the control unit O70 obtains an analysis map based on an analysis result, and stores it in the memory O72. Then, the control unit O70 displays the analysis map on the moving image of the fundus front image that is renewed as needed (see FIG. 16).

For example, the control unit O70 superimposes an analysis map M on a fundus front image F through image processing, and associates the analysis map M with the fundus front image F. Then, the control unit O70 controls the monitor O75 to display a superimposed image SI of the analysis map M and the fundus front image F. At this time, it is also preferable that the control unit O70 controls the monitor O75 to display the analysis map M and the fundus front image F separately.

<Superimposed Display Using OCT Front Image>

The control unit O70 generates an OCT front image from the three-dimensional tomographic image that is used in the analysis, and associates the generated OCT front image with the analysis map, whereby the data on the generated OCT front image and the data on the analysis map can be corresponded to each other based on a pixel-to-pixel relation.

Then, the control unit O70 performs matching of the generated OCT front image with the live fundus front image that is obtained as the moving image by the front observation optical system O200, and adjusts a relative position of the analysis map and the fundus front image.

At this time, the control unit O70 establishes the OCT fundus image, which is associated with the analysis map, as a reference image, and detects the relative position between the OCT fundus image and the fundus front image that is obtained as needed. Then, the control unit O70 corrects a display position of the analysis map based on a detection result so that a corresponding relation between the fundus portion and the analysis map coincides even if the eye moves.

For example, the control unit O70 moves the analysis map based on a positional deviation amount of the detected eye through image processing and corrects the display position by the amount, whereby the analysis map that is kept constant on the fundus front image can be observed even if the eye moves during the observation of the front image.

The simultaneous display of the analysis map and the fundus observation image is not limited to the superimposed display. Examples thereof include parallel display, display in a same screen, and display in separate monitors. It is also preferable that the control unit O70 controls the monitor O75 to display a front still image obtained in advance (e.g., a color still image obtained by a fundus camera), on which the analysis map is superimposed. It is also preferable that the control unit O70 controls the monitor O75 to display a front still image of a wide range obtained in advance (e.g., a panoramic still image obtained by a fundus camera), on which a display that indicates an obtainment position of the three-dimensional tomographic image (e.g., a line of a rectangular shape) is provided. The front still image of the wide range has a larger photographing range than the live fundus observation image.

<Extraction and Display of Tomographic Image Corresponding to Abnormal Portion>

The control unit O70 controls the monitor O75 to display a tomographic image corresponding to an abnormal portion using the analysis result of the fundus Ef based on the tomographic image. In a typical manner, the control unit O70 controls the monitor O75 to display the superimposed image SI, and display a tomographic image corresponding to the portion determined as an abnormal portion.

The control unit O70 extracts an image corresponding to a cross-section surface of the abnormal portion based on the positional information on the abnormal portion specified as described above. Then, the control unit O70 forms the superimposed image SI and tomographic images Tg1 and Tg2 corresponding to the abnormal portions on the analysis map, and controls the monitor O75 to display them at the same time (see FIG. 16). Examples of the tomographic image display include thumbnail display.

Described in the present embodiments is the configuration that the superimposed image SI and the tomographic images corresponding to the abnormal portions on the analysis map are displayed at the same time on the same screen of the same monitor; however, the present invention is not limited to this configuration. For example, a configuration is preferable such that a plurality of monitors are each provided for the images.

After extracting the tomographic image based on the three-dimensional tomographic image that is used in the analysis, the control unit O70 extracts the tomographic image corresponding to the abnormal portion every time the three-dimensional tomographic image is renewed as needed, and renews the display of the tomographic image. Thus, the tomographic image corresponding to the abnormal portion is displayed as a moving image.

Figure 16:
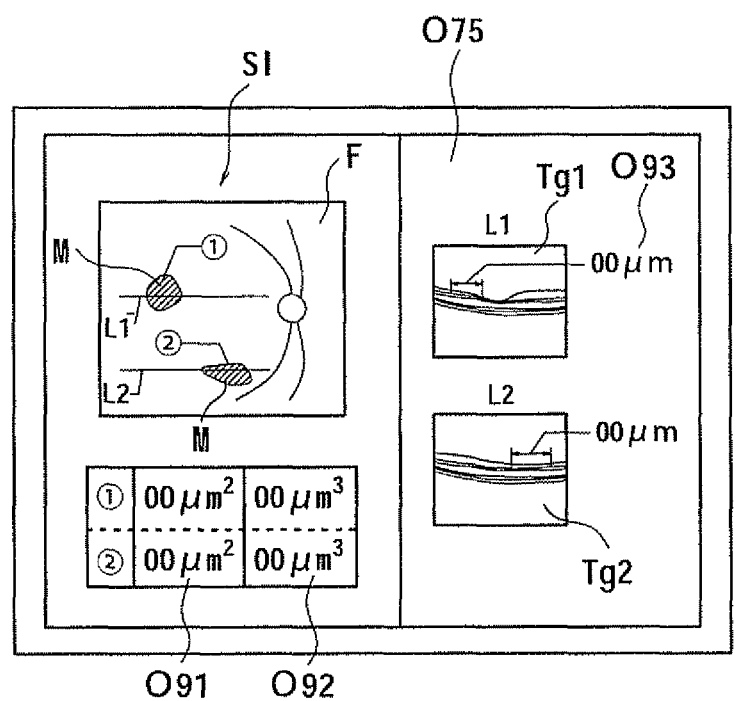
FIG. 16 is a view showing an example of a superimposed image and a tomographic image corresponding to an abnormal portion, which are displayed on a monitor.

For example, the control unit O70 displays a tomographic image corresponding to one line with respect to one abnormal portion (e.g., L1 with respect to a region of the abnormal portion shown in FIG. 16 (i.e., the region is the encircled number 1 on the front image F in FIG. 16), L2 with respect to a region of the abnormal portion shown in FIG. 16 (i.e., the region is the encircled number 2 on the front image F in FIG. 16)). The control unit O70 extracts the tomographic image of a portion, which has a largest difference from a normal eye, within the region of one abnormal portion.

It is also preferable that the control unit O70 analyzes with time the three-dimensional tomographic image that is obtained with time, and then renews the map display, the superposed display of the map and the front image, or the display of the tomographic image corresponding to the abnormal portion based on an analysis result obtained with time. In this case, the analysis and the renewal do not need to be performed in accordance with a frame rate, and it is essential only that the control unit O70 should perform renewal processing in accordance with the time necessary for the analysis. Thus, the change in the abnormal portion can be recognized. It is also preferable that the control unit O70 performs the analysis and the renewal processing at established time intervals.

It is also preferable that when the position on the fundus at which the three-dimensional tomographic image is picked up is changed, the control unit O70 analyzes a three-dimensional tomographic image that is obtained after the position is changed. The change of the position can be performed with the use of the optical scanner O108 and the fixation target projection unit O300.

Then, the control unit O70 performs at least one of specification of an abnormal portion based on the three-dimensional tomographic image that is obtained at the new position, and making-up of an analysis map, and then renews the map display, the superposed display of the map and the front image, and the display of the tomographic image corresponding to the abnormal portion. Thus, the examiner can check an analysis result corresponding to the renewed position.

When the analysis map is renewed in the manner described above, if a portion of the position before the position is changed overlaps the position after the position is changed, it is also preferable that the control unit O70 makes an analysis map, which corresponds to the overlapping portion of the position before the position is changed, superimpose on the front image.

If the OCT optical system O100 functions also as the front observation optical system O200, the control unit O70 controls the optical scanner O108 to scan the measurement light two-dimensionally, and obtains a tomographic image and a front image as a moving image based on the photo-receiving signal outputted from the photodetector O120. Then, the control unit O70 controls the monitor O75 to display the obtained tomographic image and front image. At this time, because obtained is the three-dimensional tomographic image corresponding to two-dimensional scan, it is also preferable that the control unit O70 extracts a tomographic image corresponding to the abnormal portion based on the positional information on the abnormal portion, and controls the monitor O75 to display the extracted tomographic image.

<Display of Measurement Information>

The control unit O70 measures measurement information on the abnormal portion (e.g., a size, an area, a volume) through image processing, and displays the measurement information together with the tomographic image on the same screen of the monitor O75. The control unit O70 displays the measurement information on the region that is determined as an abnormal portion in the fundus front image and the tomographic image.

For example, the control unit O70 displays the area and the volume of the abnormal portion as the measurement information by associating them with the fundus front image (the display includes superimposed display). In addition, the control unit O70 displays a width of the abnormal portion as the measurement information by associating it with the fundus tomographic image (the display includes superimposed display).

When displaying the area of the abnormal portion as the measurement information, the control unit O70 makes up area information O91 that indicates the area of the abnormal portion in accordance with the region displayed in the specific color as the abnormal portion. The area is calculated by counting the number of pixels in the portion displayed in the specific color. It is also preferable that the control unit O70 obtains the area information O91 from the analysis map, or from the analysis result of the three-dimensional tomographic image.

In addition, the control unit O70 makes up volume information O92 that indicates the volume of the region on which the area information described above is made up. The volume is calculated by obtaining information in a depth direction corresponding to the region of which the area is calculated, and using the area and the information in the depth direction.

Then, the control unit O70 makes the area information O91 and the volume information O92 in addition to the analysis map superimpose on the fundus front image, and controls the monitor O75 to display them.

In addition, the control unit O70 calculates the width in the transverse direction of the region corresponding to the area information O91 and the volume information 92 on the fundus image corresponding to the abnormal portion by using the analysis result, and obtains width information O93. Then, the control unit O70 controls the monitor O75 to display the width information O93 on the tomographic image.

Described above is the configuration to display the measurement information (the width information in the present embodiments) on the tomographic image; however the present invention is not limited to this configuration. It is also preferable that when the determination of a normal/abnormal portion is performed by detecting the thickness of a retinal optic nerve fiber layer, a retinal optic nerve fiber layer that corresponds to a region that is determined as an abnormal portion is colored in a specific color, and a tomographic image that is colored is displayed.

The configuration described above allows observation of the abnormal portion on the fundus image and the tomographic image without analyzing again the data that is once stored, which allows smooth measurement of a lesion. In addition, the specification of the abnormal portion can prevent photographing by mistake a region that is not a subject to be photographed.

Conventionally, the manipulation for the obtainment operation and the manipulation necessary for the analysis processing are performed at different times, so that changeover between the manipulation for the obtainment operation and the manipulation necessary for the analysis processing takes a lot of trouble. In the present invention, on the other hand, the obtainment operation of the tomographic image and the analysis processing of the obtained tomographic image are performed at a time, which allows the obtainment of the tomographic image and the analysis processing to be performed smoothly.

In addition, because the examiner can check the abnormal portion on the spot, more precise information can be obtained, which allows easy selection of examinations to be performed in the next step.

Described in the present embodiments is the configuration that the tomographic image corresponding to one scan line is displayed with respect to one abnormal portion on the monitor O75; however, the present invention is not limited to this configuration. It is also preferable that tomographic images corresponding to multi scan lines are displayed.

Described in the present embodiments is the configuration that in extracting a tomographic image corresponding to one line with respect to a region of one abnormal portion, a tomographic image corresponding to a line that has the largest difference from the normal eye is extracted; however, the present invention is not limited to this configuration. It is also preferable that a tomographic image corresponding to a line that passes through the center of the abnormal region is extracted. It is also preferable that a tomographic image corresponding to a line that is closest to a macular is extracted. It is also preferable that the examiner can arbitrarily select establishment of a line to be displayed.

Described in the present embodiments is the configuration that the analysis is started by the manipulation (input) of the photographing switch; however, the present invention is not limited to this configuration. It is also preferable that when starting to make the eye show up on the monitor O75 with the use of the apparatus (at the stage of alignment), the control unit O70 performs the analysis and controls the monitor O75 to display the analysis map and the measurement information. It is also preferable that the control unit O70 starts the analysis at the stage of adjusting the optical path length with the fundus Ef and obtaining the fundus tomographic image.

Described in the present embodiments is the configuration that the scan for obtaining the three-dimensional tomographic image is performed as needed; however, the present invention is not limited to this configuration. It is also preferable to have a configuration such that a scanning position and a scanning pattern of the measurement light with respect to the fundus can be established on the front observation image that is displayed as a moving image. In this case, the scanning position and the scanning pattern are established by the examiner or automatic control after obtainment of the three-dimensional tomographic image. For example, the tomographic image is obtained in different scan methods such as a circle scan method and a multi scan method in the region where the abnormal portion is detected through the analysis of the three-dimensional tomographic image.

As a manner for specifying an abnormal portion, it is also preferable that a portion of which a measurement result has a large difference from a value in the normal eye database is specified as an abnormal portion. For example, the control unit specifies a portion of which a measurement result has a largest difference from a value in the normal eye database as an abnormal portion, controls the monitor O75 to display a tomographic image of the abnormal portion. Thus, observation as to whether the fundus has an abnormal portion or not can be performed smoothly.

Described in the present embodiments is the ophthalmic photographing apparatus that is used in the fundus photographing apparatus; however, the present invention is not limited hereto. For example, the ophthalmic photographing apparatus of the present embodiments can be used in an apparatus for photographing an anterior segment of an eye. When a tomographic image of an anterior segment of the eye is analyzed, the control unit calculates positional information/intensity information on a tissue of the anterior segment in the obtained three-dimensional tomographic image. Then, the control unit measures corneal surface/back-surface curvature distribution, corneal thickness distribution, crystalline lens anterior surface/posterior surface curvature distribution, crystalline lens thickness distribution, anterior chamber depth distribution, and an inclined angle of gonion based on the positional information. For example, an abnormal portion is specified based on whether the inclined angle of gonion of the eye E goes beyond a given permissible range or not.

Described in the present embodiments is the configuration that the tomographic image corresponding to the abnormal portion that is specified through analysis processing is extracted from the three-dimensional tomographic image, and the extracted tomographic image is displayed on the monitor O75 together with the front observation image; however, the present invention is not limited to this configuration. It is also preferable that the control unit O70 controls the monitor O75 to display the extracted tomographic image alone, or together with another image.

It is also preferable that the control unit O70 controls the monitor O75 to display both a still image of the extracted tomographic image, and the tomographic image that is obtained as a moving image, at the same time. In addition, the extracting processing of the tomographic image corresponding to the abnormal portion is useful even if it is not performed live. For example, such the extracting processing is useful in specifying an abnormal portion.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic photographing apparatus comprising:
an optical coherence tomography device that comprises an optical scanner for setting a photographing position on an examinee's eye, and is configured to obtain a tomographic image of the examinee's eye;
a driving control unit configured to control driving of the optical scanner and scan measurement light two-dimensionally on the eye, and obtain a three-dimensional image of the eye:
an image processing unit configured to analyze the three-dimensional image;
a display control unit configured to control a monitor to display:
an observation optical system configured to obtain a front observation image of the examinee's eye as a moving image; and
an operation unit configured to be operated by an examiner, wherein:
the optical coherence tomography device comprises an optical coherence tomography device configured to obtain a tomographic image of a fundus of the examinee's eye,
the image processing unit is configured to detect information on layers of the fundus in the three-dimensional image of the fundus through image processing, and make up an analysis map indicating two-dimensional distribution on the fundus layers,
the display control unit controls the monitor to display at the same time, the analysis map, and the moving image of the front observation image obtained by the observation optical system; and
the driving control unit is configured to control the optical coherence tomography device based on a signal from the operation unit, wherein a position on the examinee's eye at which the tomographic image is to be picked up is changeable by using the moving image of the front observation image and the analysis map.

2. The ophthalmic photographing apparatus according to claim 1, wherein the display control unit controls the monitor to display the moving image of the front observation image on which the analysis map is superimposed.

3. The ophthalmic photographing apparatus according to claim 1, wherein the image processing unit is configured to generate an OCT front image from the three-dimensional image that is used in the analysis, perform matching of the generated OCT front image with the fundus front image that is obtained by the observation optical system, and adjust a relative position of the analysis map and the fundus front image.

4. An ophthalmic photographing apparatus comprising:
an optical coherence tomography device that comprises an optical scanner for setting a photographing position on an examinee's eye, and is configured to obtain a tomographic image of the examinee's eye;

an observation optical system configured to obtain a front observation image of the examinee's eye as a moving image;

a driving control unit configured to control driving of the optical scanner and scan measurement light two-dimensionally on the eye, and obtain a three-dimensional image of the eye;

an image processing unit configured to analyze the three-dimensional image, and make up an analysis map based on a result of the analysis; and a display control unit configured to control a monitor to display the analysis map and the moving image of the front observation image obtained by the observation optical system; and an operation unit configured to be operated by an examiner, wherein the driving control unit is configured to control the optical coherence tomography device based on a signal from the operation unit, wherein a position on the examinee's eye at which the tomographic image is to be picked up is changeable by using the moving image of the front observation image and the analysis map.

5. The ophthalmic photographing apparatus according to claim 4, wherein the display control unit controls the monitor to display the moving image of the front observation image on which the analysis map is superimposed.

6. The ophthalmic photographing apparatus according to claim 4, wherein the image processing unit is configured to generate an OCT front image from the three-dimensional image that is used in the analysis, perform matching of the generated OCT front image with the fundus front image that is obtained by the observation optical system, and adjust a relative position of the analysis map and the fundus front image.

7. The ophthalmic photographing apparatus according to claim 4, wherein the image processing unit starts analysis of the three-dimensional image triggered by obtainment of the three-dimensional image.

* * * * *